US008852588B2

(12) United States Patent
Chang

(10) Patent No.: US 8,852,588 B2
(45) Date of Patent: Oct. 7, 2014

(54) TREATING ALLERGIC AIRWAY DISORDERS USING ANTI-IL-20 RECEPTOR ANTIBODIES

(75) Inventor: Ming-Shi Chang, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 13/568,666

(22) Filed: Aug. 7, 2012

(65) Prior Publication Data

US 2014/0044715 A1    Feb. 13, 2014

(51) Int. Cl.
A61K 39/395 (2006.01)
C07K 16/24 (2006.01)

(52) U.S. Cl.
USPC .......... 424/130.1; 424/133.1; 424/135.1; 424/143.1; 514/1.7; 514/826; 530/387.1

(58) Field of Classification Search
None
See application file for complete search history.

(56) References Cited

U.S. PATENT DOCUMENTS

| | | | |
|---|---|---|---|
| 5,585,089 | A | 12/1996 | Queen et al. |
| 5,605,690 | A | 2/1997 | Jacobs et al. |
| 5,888,510 | A | 3/1999 | Kishimoto et al. |
| 7,119,191 | B2 | 10/2006 | Conklin et al. |
| 7,122,632 | B2 | 10/2006 | Foster et al. |
| 7,151,166 | B2 | 12/2006 | Conklin et al. |
| 7,189,394 | B2 | 3/2007 | Thompson et al. |
| 7,393,684 | B2 | 7/2008 | Xu et al. |
| 7,435,800 | B2 | 10/2008 | Chang |
| 7,611,705 | B2 | 11/2009 | Chang |
| 7,786,274 | B2 | 8/2010 | Chang |
| 7,837,994 | B2 | 11/2010 | Chang |
| 8,012,478 | B2 | 9/2011 | Chang |
| 8,206,712 | B2 | 6/2012 | Chang |
| 8,287,861 | B2 | 10/2012 | Pass et al. |
| 8,454,956 | B2 | 6/2013 | Chang |
| 2002/0151532 | A1 | 10/2002 | Kagan et al. |
| 2003/0148955 | A1 | 8/2003 | Pluenneke |
| 2004/0009168 | A1 | 1/2004 | Kaisheva et al. |
| 2004/0191243 | A1 | 9/2004 | Chen et al. |
| 2004/0197324 | A1 | 10/2004 | Liu et al. |
| 2004/0235728 | A1 | 11/2004 | Stoch et al. |
| 2004/0235808 | A1 | 11/2004 | Wang |
| 2005/0003475 | A1 | 1/2005 | Foster et al. |
| 2005/0136004 | A1 | 6/2005 | Xu et al. |
| 2005/0142108 | A1 | 6/2005 | Grunig et al. |
| 2005/0143333 | A1 | 6/2005 | Richards et al. |
| 2005/0170468 | A1 | 8/2005 | Xu et al. |
| 2006/0134756 | A1 | 6/2006 | Xu et al. |
| 2006/0142550 | A1 | 6/2006 | Chang |
| 2006/0177447 | A1 | 8/2006 | Xu |
| 2006/0188476 | A1 | 8/2006 | Olsen et al. |
| 2006/0269551 | A1 | 11/2006 | Thompson et al. |
| 2007/0053871 | A1 | 3/2007 | Li et al. |
| 2007/0116700 | A1 | 5/2007 | Liu et al. |
| 2008/0247945 | A1 | 10/2008 | Xu et al. |
| 2008/0311115 | A1 | 12/2008 | Chang |
| 2009/0048432 | A1 | 2/2009 | Chang |
| 2009/0312236 | A1 | 12/2009 | Beals et al. |
| 2011/0064731 | A1 | 3/2011 | Chang |
| 2011/0091475 | A1 | 4/2011 | Pass et al. |
| 2011/0256093 | A1 | 10/2011 | Chang |
| 2011/0305698 | A1 | 12/2011 | Chang |
| 2011/0305699 | A1 | 12/2011 | Chang |

FOREIGN PATENT DOCUMENTS

| | | |
|---|---|---|
| EP | 2 050 458 | 4/2009 |
| WO | WO 92/07584 A1 | 5/1992 |
| WO | WO 99/03982 A1 | 1/1999 |
| WO | WO 99/27103 A1 | 6/1999 |
| WO | WO 01/46261 A1 | 6/2001 |
| WO | WO 03/051384 A1 | 6/2003 |
| WO | WO 2004/085475 A2 | 10/2004 |
| WO | WO 2005/052000 A2 | 6/2005 |
| WO | WO 2006/086396 A2 | 8/2006 |
| WO | WO 2007/081465 A2 | 7/2007 |
| WO | WO 2008/009545 A1 | 1/2008 |
| WO | WO 2008/009645 A1 | 1/2008 |
| WO | WO 2008/045563 A1 | 4/2008 |
| WO | WO 2008/086395 A2 | 7/2008 |
| WO | WO 2008/157161 A1 | 12/2008 |
| WO | WO 2009/077483 A1 | 6/2009 |
| WO | WO 2009/103113 A1 | 8/2009 |
| WO | WO 2010/000721 A1 | 1/2010 |
| WO | WO 2010/072691 A1 | 7/2010 |
| WO | WO 2011/104381 A2 | 9/2011 |
| WO | WO 2011/130611 A2 | 10/2011 |
| WO | WO 2011/147921 A1 | 12/2011 |

OTHER PUBLICATIONS

Brummell et al. Biochemistry, 1993, vol. 32, pp. 1180-1187.*
Kobayashi et al. Protein Engineering, 199, vol. 12, pp. 879-844.*
Burks et al. PNAS, 1997, vol. 94, pp. 412-417.*
Jang et al. Molec. Immunol, 1998, vol. 35, pp. 1207-1217.*
Brorson et al. J. Immunol, 1999, vol. 163, pp. 6694-6701.*
Coleman Research in Immunol, 1994, vol. 145, pp. 33-36.*
[No Author Listed] Stroke. Mayo Clinic. http://www.MayoClinic.com/. Last accessed on Sep. 29, 2009. 3 pages.
[No Author Listed] Stroke. Treatment and Drugs. Mayo Clinic. http://www.MayoClinic.com/. Last accessed on Sep. 29, 2009. 2 pages.
Alanara et al., Expression of IL-10 family cytokines in rheumatoid arthritis: elevated levels of IL-19 in the joints. Scand J Rheumatol. Mar. 2010;39(2):118-26.
Balmaña et al., ESMO Guidelines Working Group. BRCA in breast cancer: ESMO clinical recommendations. Ann Oncol. May 2009;20 Suppl. 4: 19-20.
Baselga, The EGFR as a target for anticancer therapy—focus on cetuximab. Eur J Cancer. Sep. 2001;37 Suppl 4:S16-22.

(Continued)

Primary Examiner — Bridget E Bunner
Assistant Examiner — Fozia Hamud
(74) Attorney, Agent, or Firm — Wolf, Greenfield & Sacks, P.C.

(57) ABSTRACT

Treatment of an allergic airway disorder (e.g., asthma or bronchial airway obstruction) using anti-IL-20R1 antibodies such as mAb51D, mAb7GW, or functional variants thereof.

16 Claims, 7 Drawing Sheets

(56) References Cited

OTHER PUBLICATIONS

Beiboer et al., Guided selection of a pan carcinoma specific antibody reveals similar binding characteristics yet structural divergence between the original murine antibody and its human equivalent. J Mol Biol. Feb. 25, 2000;296(3):833-49.

Blumberg et al., Interleukin 20: discovery, receptor identification, and role in epidermal function. Cell. Jan. 12, 2001;104(1):9-19.

Body et al., A study of the biological receptor activator of nuclear factor-kappaB ligand inhibitor, denosumab, in patients with multiple myeloma or bone metastases from breast cancer. Clin Cancer Res. Feb. 15, 2006;12(4):1221-8.

Chang et al., Crystal structure of interleukin-19 defines a new subfamily of helical cytokines. J Biol Chem. Jan. 31, 2003;278(5):3308-13. Epub Oct. 25, 2002.

Chen et al., IL-20 is regulated by hypoxia-inducible factor and up-regulated after experimental ischemic stroke. J Immunol. Apr. 15, 2009;182(8):5003-12.

Chuntharapai et al., Generation of monoclonal antibodies to chemokine receptors. Methods Enzymol. 1997;288:15-27.

Cunningham et al., High-resolution epitope mapping of hGH-receptor interactions by alanine-scanning mutagenesis. Science. Jun. 2, 1989;244(4908):1081-5.

D'Andrea et al., Interleukin 10 (IL-10) inhibits human lymphocyte interferon gamma-production by suppressing natural killer cell stimulatory factor/IL-12 synthesis in accessory cells. J Exp Med. Sep. 1, 1993;178(3):1041-8.

Dumont, IL-10-related cellular cytokines and their receptors: new targets for inflammation and cancer therapy. Expert Opin Ther Patents. Mar. 2004;14(3):281-99.

Dumoutier et al., Cutting edge: Stat activation by IL-19, IL-20 and mda-7 through IL-20 receptor complexes of two types. J Immunol. Oct. 1, 2001;167(7):3545-9.

Egermann et al., Direct adenoviral transfer of bone morphogenetic protein-2 cDNA enhances fracture healing in osteoporotic sheep. Hum Gene Ther. May 2006;17(5):507-17.

Est From Incyte Pharmaceuticals Inc., INC819592. 1996. 1 page.

Fox et al., Breast cancer angiogenesis. Breast Cancer Resear. 2007;9(216):1-11.

Genbank Submission, Accession No. AAK84423; Rieder et al.; Aug. 9, 2001. Last accessed on Jul. 18, 2012 at http://www.ncbi.nlm.nih.gov/protein/15128211. 1 page.

George et al., Current Methods in Sequence Comparison. Macromolecular Sequencing and Synthesis. 1988;127-49.

Goffe et al., Etanercept: An overview. J Am Acad Dermatol. Aug. 2003;49(2 Suppl):S105-11.

Harlow et al., Antibodies a Laboratory Manual. Cold Springs Harbor Laboratory. 1988;76.

Heuzé-Vourc'h et al., IL-20, an anti-angiogenic cytokine that inhibits COX-2 expression. Biochem Biophys Res Commun Jul. 29, 2005;333(2):470-5.

Holliger et al., "Diabodies": small bivalent and bispecific antibody fragments. Proc Natl Acad Sci U S A. Jul. 15, 1993;90(14):6444-8.

Hor et al., The T-cell lymphokine interleukin-26 targets epithelial cells through the interleukin-20 receptor 1 and interleukin-10 receptor 2 chains. J Biol Chem. Aug. 6, 2004;279(32):33343-51. Epub Jun. 3, 2004.

Howe et al., Cyclooxygenase-2: a target for the prevention and treatment of breast cancer. Endocr Relat Cancer. Jun. 2001;8(2):97-114.

Hsieh et al., Interleukin-20 promotes angiogenesis in a direct and indirect manner Genes Immun.Apr. 2006;7(3): 234-52.

Hsing et al., The distribution of interleukin-19 in healthy and neoplastic tissue. Cytokine. Nov. 2008;44(2):221-8. Epub Sep. 21, 2008.

Hsing et al., Tissue microarray analysis of interleukin-20 expression. Cytokine. Jul. 2006;35(1-2):44-52. Epub Sep. 5, 2006.

Hsu et al., Anti-IL-20 monoclonal antibody inhibits the differentiation of osteoclasts and protects against osteoporotic bone loss. J Exp Med. Aug. 29, 2011;208(9):1849-61. Epub Aug. 15, 2011.

Hsu et al., Function of interleukin-20 as a proinflammatory molecule in rheumatoid and experimental arthritis. Arthritis Rheum. Sep. 2006;54(9):2722-33.

Hunt et al., Ultraviolet B light stimulates interleukin-20 expression by human epithelial keratinocytes. Photochem Photbiol. Sep./Oct. 2006;82:1292-1300.

Incyte Pharmaceuticals Inc., INC4304592, Jul. 8, 1998. 1 page.

Jung et al., Analysis of the expression profiles of cytokines and cytokine-related genes during the progression of breast cancer growth in mice. Oncol Rep. Nov. 2009;22(5):1141-7.

Kataja et al., ESMO Guidelines Working Group. Primary breast cancer: ESMO clinical recommendations for diagnosis, treatment and follow-up. Ann Oncol. May 2009;20 Suppl 4:10-4.

Klimka et al., Human anti-CD30 recombinant antibodies by guided phage antibody selection using cell panning. Br J Cancer. Jul. 2000;83(2):252-60.

Kragstrup et al., The expression of IL-20 and IL-24 and their shared receptors are increased in rheumatoid arthritis and spondyloarthropathy. Cytokine. Jan. 2008;41(1):16-23. Epub Dec. 3, 2007.

Li et al., Interleukin-20 induced cell death in renal epithelial cells and was associated with acute renal failure. Genes Immun. Jul. 2008;9(5):395-404. Epub May 22, 2008.

Liao et al., IL-19 induced Th2 cytokines and was up-regulated in asthma patients. J Immunol. 2004;173:6712-8.

Lonberg, Human monoclonal antibodies from transgenic mice. Handbook Exp Pharmacol. 2008;(181):69-97.

Mikayama et al., Molecular cloning and functional expression of a cDNA encoding glycosylation-inhibiting factor. Proc Natl Acad Sci U S A. Nov. 1, 1993;90(21):10056-60.

Nelson et al., U.S. Preventive Services Task Force. Screening for breast cancer: an update for the U.S. Preventive Services Task Force. Ann Intern Med. Nov. 17, 2009;151(10):727-37, W237-42.

Otkjaer et al., The dynamics of gene expression of interleukin-19 and interleukin-20 and their receptors in psoriasis. Br J Dermatol. Nov. 2005;153(5):911-8.

Parrish-Novak et al., Interleukins 19, 20, and 24 signal through two distinct receptor complexes. Differences in receptor-ligand interactions mediate unique biological functions. J Biol Chem. Dec. 6, 2002;277(49):47517-23. Epub Sep. 25, 2002.

Parrish-Novak et al., Overlapping Ligand Specificities but Divergent Function in the IL-20 Sub family. J Interferon Cytokine Res. 2002;22. Supplement 46.

Rich, IL-20: a new target for the treatment of inflammatory skin disease. Expert Opin Ther Targets. Apr. 2003;7(2):165-74.

Rohovsky et al., Growth Factors and Angiogenesis in Wound Healing. Growth Factors Wound Healing. Ziegler et al., eds. 1997:8-26.

Romer et al., Epidermal overexpression of interleukin-19 and -20 mRNA in psoriatic skin disappears after short-term treatment with cyclosporine a or calcipotriol. J Invest Dermatol. Dec. 2003;121(6):1306-11.

Sabat et al., IL-19 and IL-20:two novel cytokines with importance in inflammatory diseases. Expert Opinion Therapeutic Targets. May 2007;11(5):p601-12. Abstract Only.

Saidenberg-Kermanac'h et al., TNF-alpha antibodies and osteoprotegerin decrease systemic bone loss associated with inflammation through distinct mechanisms in collagen-induced arthritis. Bone. Nov. 2004;35(5):1200-7.

Sakurai et al., Expression of IL-19 and its receptors in RA: potential role for synovial hyperplasia formation. Rheumatology (Oxford). Jun. 2008;47(6):815-20. Epub Apr. 8, 2008.

Salinas et al., Understanding and modulating opalescence and viscosity in a monoclonal antibody formulation. J Pharm Sci. Jan. 2010;99(1):82-93.

Seriolo et al., Bone metabolism changes during anti-TNF-alpha therapy in patients with active rheumatoid arthritis. Ann N Y Acad Sci. Jun. 2006;1069:420-7.

Siderov et al., Care with intrathecal trastuzumab. Lancet Oncology. 2006;7(11):888.

Slavin, Cytokines and Tissue Repair. J Immunol Immunopharmacol. 1997;17(1):25-9.

Staelens et al., Humanization by variable domain resurfacing and grafting on a human IgG4, using a new approach for determination of

(56) References Cited

OTHER PUBLICATIONS non-human like surface accessible framework residues based on homology modelling of variable domains. Mol Immunol. Mar. 2006;43(8):1243-57. Epub Aug. 22, 2005.

Stenderup et al., Interleukin 20 Controls Psoriasis Induction and Maintenance. British Journal of Dermatology. 2006;154:11-35.

Stenderup et al., Interleukin-20 plays a critical role in maintenance and development of psoriasis in the human xenograft transplantation model. Br J Dermatol. Feb. 2009;160(2):284-96. Epub Oct. 20, 2008.

Sugerman et al., Current concepts in oral cancer. Aust Dent J. 1999;44(3):147-56.

Voet et al., Biochemistry. John Wiley & Sons, Inc. New York. 1990:126-8, 228-34.

Wang et al., Prominent production of IL-20 by CD68+/CD11c+ myeloid-derived cells in psoriasis: Gene regulation and cellular effects. J Invest Dermatol. Jul. 2006;126(7):1590-9. Epub Apr. 27, 2006.

Wei et al., Detection of IL-20 and its receptors on psoriatic skin. Clin Immunol. Oct. 2005;117(1): 65-72.

Wei et al., IL-20: biological functions and clinical implications. J Biomed Sci. Sep. 2006;13(5):601-12. Epub May 16, 2006. Review.

Williams et al., Tumor angiogenesis as a prognostic factor in oral cavity tumors. Am J Surg. Nov. 1994;168(5):373-80.

Wuyts et al., Isolation of the CXC chemokines ENA-78, GRO alpha and GRO gamma from tumor cells and leukocytes reveals NH2-terminal heterogeneity. Functional comparison of different natural isoforms. Eur J Biochem. Mar. 1999;260(2):421-9.

Zheng et al., Human interleukin 24 (MDA-7/IL-24) protein kills breast cancer cells via the IL-20 receptor and is antagonized by IL-10. Cancer Immunol Immunother. Feb. 2007;56(2):205-15. Epub May 19, 2006.

Zheng et al., Role of cytokine therapy in the treatment of psoriasis. Drug Discov Today: Ther Strat. 2007;4(1):25-31.

\* cited by examiner

A.

B.

A.

B.

C.

A.

B.

US 8,852,588 B2

TREATING ALLERGIC AIRWAY DISORDERS USING ANTI-IL-20 RECEPTOR ANTIBODIES

BACKGROUND OF THE INVENTION

IL-20 receptor is a dimeric complex containing subunits IL-20R1 and IL-20R2 (also known as RA and RB). Human IL-20R1 and IL-20R2 are disclosed under GenBank accession numbers NP_055247 (protein)/NM_014432.2 (mRNA) and NP_653318 (protein)/NM_144717 (mRNA), respectively. This IL-20 receptor is a common receptor for three functionally different cytokines, i.e., IL-19, IL-20, and IL-24, suggesting that it can mediate different signaling pathways when triggered by different cytokines.

Allergic airway diseases are allergic diseases of the airways, including asthma, allergic rhinitis, and allergic pneumonia. Asthma is a common chronic inflammatory disease of the airways characterized by reversible airflow obstruction, bronchospasm, and other recurring symptoms. Asthma patients often suffer from wheezing, coughing, chest tightness, and shortness of breath. While long-term control medications and quick-relief medications are available for treating asthma, there is currently no cure for this disease.

SUMMARY OF THE INVENTION

The present disclosure is based on the unexpected discoveries that (a) IL-20 receptor R1 (IL-20R1) knock-out mice were protected from developing asthma when challenged with allergens, and (b) an antibody specifically binding to human IL-20R1 successfully reduced the levels of IL-13 and IgE in mice challenged with allergen Der P and reduced the amounts of eosinophil and neutrophil cells in the bronchoalveolar lavage fluid (BALF) of such mice. These results suggest that antibodies binding to IL-20 receptor, e.g., anti-IL-20R1 antibodies, can reduce allergic responses in the airway, thereby being effective in treating allergic airway diseases such as asthma.

Accordingly, disclosed herein are methods for treating an allergic airway disorder (e.g., asthma or bronchial airway obstruction), the method comprising administering to a subject in need thereof (e.g., a human patient having, suspected of having, or at risk for the disorder) an effective amount of an antibody that binds an IL-20 receptor and neutralizes its activity. Such an antibody can be an anti-IL-20R1 antibody.

In some embodiments, the anti-IL-20R1 can comprise: (a) a heavy chain variable region ($V_H$) that includes a $V_H$ CDR1, a $V_H$ CDR2, and a $V_H$ CDR3 at least 85% (e.g., 90%, 95, or 98%) identical to the $V_H$ CDR1, $V_H$ CDR2, and $V_H$ CDR3 of monoclonal antibody mAb51D or mAb7GW, respectively, and (b) a light chain variable region ($V_L$) that includes a $V_L$ CDR1, a $V_L$ CDR2, and a $V_L$ CDR3 at least 85% (e.g., 90%, 95%, or 98%) identical to the $V_L$ CDR1, $V_L$ CDR2, and $V_L$ CDR3 of mAb51D or mAb7GW, respectively.

In other embodiments, the anti-IL-20R1 antibody can comprise (a) a $V_H$ that includes up to 5 amino acid variations (e.g., 1, 2, 3, 4, or 5 amino acid residue substitutions) in $V_H$ CDRs as compared to the $V_H$ CDRs of mAb51D or mAb7GW, and (b) a $V_L$ that includes up to 5 amino acid variations (e.g., 1, 2, 3, 4, or 5 amino acid residue substitutions) in $V_L$ CDRs as compared to the $V_L$ CDRs of mAb51D or mAb7GW.

In one example, the anti-IL-20R1 antibody comprises a $V_H$ that includes the same $V_H$ CDRs as those of mAb51D or mAb7GW, a $V_L$ that includes the same $V_L$ CDRs as those of mAb51D or mAb7GW, or both.

Any of the antibodies described herein, e.g., the anti-IL-20R1 antibody as described above, can be a full-length antibody or an antigen-binding fragment thereof, e.g., Fab, $F(ab')_2$, Fab', or Fv. Alternatively, the antibody can be a humanized antibody, a chimeric antibody, or a single-chain antibody.

Also within the scope of the present disclosure are (a) pharmaceutical compositions for use in treating an allergic airway disorder such as asthma or bronchial airway obstruction, the composition comprising any of the antibodies described herein (e.g., an anti-IL-20R1 antibody as disclosed above) and a pharmaceutically acceptable carrier, and (b) use of the just-noted pharmaceutical composition in manufacturing a medicament for treating an allergic airway disease such as asthma or bronchial airway obstruction.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are first described.

BRIEF DESCRIPTION OF THE SEQUENCES

Figure 1:
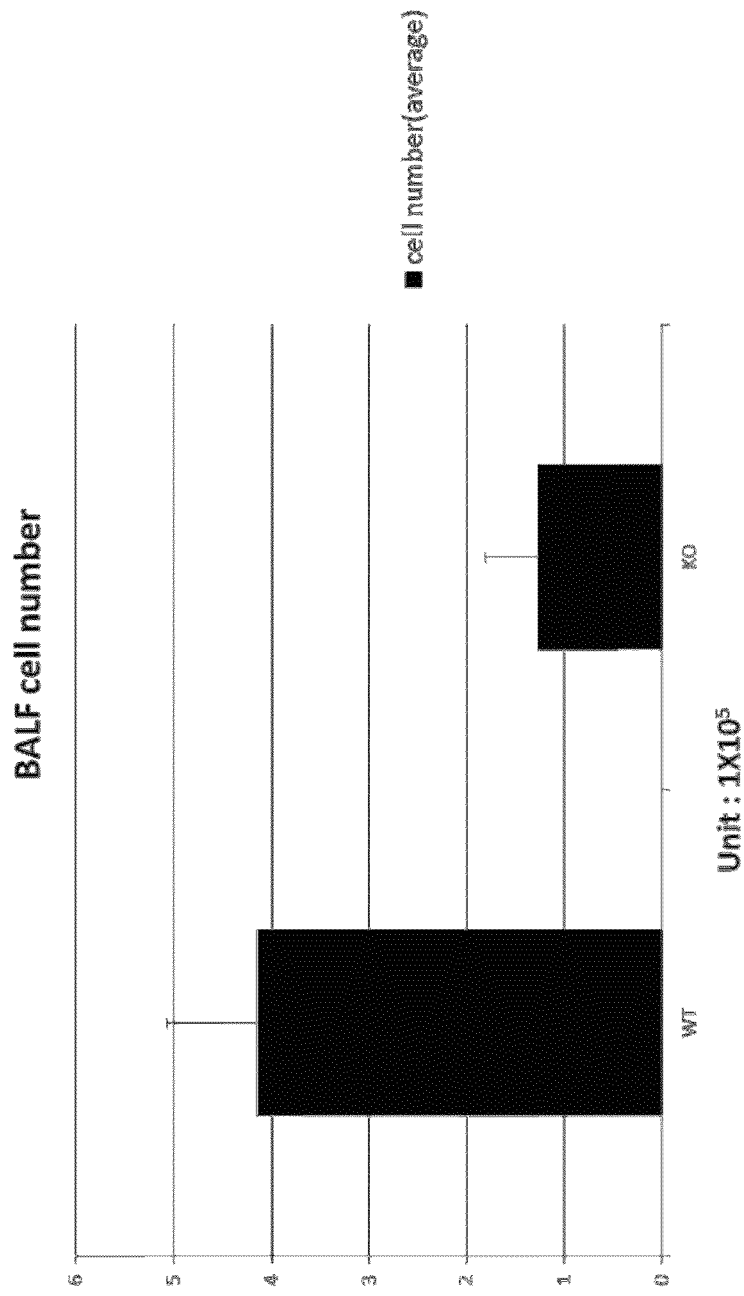
FIG. 1 is a chart showing the total cell number in the bronchoalveolar lavage fluid (BALF) of wild-type (WT) and IL-20R1-knock out (KO) mice.

SEQ ID NO:1 is the amino acid sequence of the heavy chain of monoclonal antibody mAb7GW (precursor form, which includes the signal peptide).

SEQ ID NO:2 is the nucleotide sequence encoding the heavy chain of monoclonal antibody mAb7GW (precursor form, which includes the signal peptide).

SEQ ID NO:3 is the amino acid sequence of the light chain of monoclonal antibody mAb7GW (precursor form, which includes the signal peptide).

SEQ ID NO:4 is the nucleotide sequence encoding the light chain of monoclonal antibody mAb7GW (precursor form, which includes the signal peptide).

SEQ ID NO:5 is the amino acid sequence of the heavy chain of monoclonal antibody mAb51D (precursor form, which includes the signal peptide).

SEQ ID NO:6 is the nucleotide sequence encoding the heavy chain of monoclonal antibody mAb51D (precursor form, which includes the signal peptide).

SEQ ID NO:7 is the amino acid sequence of the light chain of monoclonal antibody mAb51D (precursor form, which includes the signal peptide).

SEQ ID NO:8 is the nucleotide sequence encoding the light chain of monoclonal antibody mAb51D (precursor form, which includes the signal peptide).

DETAILED DESCRIPTION OF THE INVENTION

The present disclosure is based on the unexpected discovery that an anti-IL-20R1 antibody, which was found to interfere with both the IL-19 and the IL-20 signaling pathways, successfully suppressed allergic responses in the airway of mice challenged by an allergen. Accordingly, disclosed herein are methods for treating allergic airway diseases, such as asthma, allergic rhinitis, allergic pneumonia, and bronchial airway obstruction, with an effective amount of an anti-IL-20R1 antibody. In some embodiments, this antibody binds (e.g., specifically) human IL-20R1 and interferes with the signaling pathway mediated by IL-19 and/or IL-20.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Anti-IL-20R Antibodies

The antibodies to be used in the methods described herein includes intact (full-length) immunoglobulin molecules, e.g., IgG, IgA, IgD, IgE, and IgM, antigen binding fragments thereof, e.g., Fab, F(ab')$_2$, Fab', and Fv, and genetically engineered antibody molecules, e.g., chimeric antibody, humanized antibody, scFv (single chain antibody), dAb (domain antibody; see Ward, et. al. (1989) Nature, 341: 544), and bi-specific antibody (e.g., capable of binding to both IL-20R1 and IL-19).

In some embodiments, the antibody used in the methods described herein an antibody having the same heavy chain and light chain variable regions ($V_H$ and $V_L$) as those of monoclonal antibody mAb7GW or mAb51D, the monoclonal antibodies, an antigen-binding fragment thereof, or a functional equivalent of either mAb7GW or mAb51D. Shown below are the amino acid sequences of the heavy chains and light chains of mAb7GW and mAb51D, as well as their encoding nucleotide sequences.

```
Heavy Chain of mAb7GW:
Amino Acid Sequence
                                                                    (SEQ ID NO: 1)
M R V L I L L W L F T A F P G I L S V V Q L Q E S G P G L V K P S Q S L S L T C T V T G Y S I
      Signal peptide T S D Y A W N W I R Q F P G N R L E W M G Y I D Y S G S T K Y N P S L K S R I S V T R D
    CDR1                                        CDR2

T S K N Q F F L Q L N S V T T E D T A T Y Y C A R D F G D A Y W G Q G T L V T V S A A K
                                                  CDR3

T T P P S V Y P L A P G S A A Q T N S M V T L G C L V K G Y F P E P V T V T W N S G S L S S G V H

T F P A V L Q S D L Y T L S S S V T V P S S T W P S E T V T C N V A H P A S S T K V D K K I V P R D

C G C K P C I C T V P E V S S V F I F P P K P K D V L T I T L T P K V T C V V V D I S K D D P E V Q

F S W F V D D V E V H T A Q T Q P R E E Q F N S T F R S V S E L P I M H Q D W L N G K E F K C R

V N S A A F P A P I E K T I S K T K G R P K A P Q V Y T I P P P K E Q M A K D K V S L T C M I T D F

F P E D I T V E W Q W N G Q P A E N Y K N T Q P I M D T D G S Y F V Y S K L N V Q K S N W E A G

N T F T C S V L H E G L H N H H T E K S L S H S P G K (The italic region refers to the heavy chain
constant region.)

Nucleotide Sequence
                                                                    (SEQ ID NO: 2)
ATGAGAGTGCTGATTCTTTTGTGGCTGTTCACAGCCTTTCCTGGTATCCTGTCTGTTGTGCAGC
         Signal peptide

TTCAGGAGTCGGGACCTGGCCTGGTGAAACCTTCTCAGTCTCTGTCCCTCACCTGCACTGTCA

CTGGCTACTCAATCACCAGTGATTATGCCTGGAACTGGATCCGGCAGTTTCCAGGA
                      CDR1

AACAGACTGGAGTGGATGGGCTACATAGACTACAGTGGTAGCACTAAATACAACCCC
                        CDR2

TCTCTCAAAAGTCGAATCTCTGTCACTCGAGACACATCCAAGAACCAGTTCTTCCTGCAGTT

GAATTCTGTGACTACTGAGGACACAGCCACATATTACTGTGCAAGAGACTTTGGTG
```

ATGCTTACTGGGGCCAGGGGACTCTGGTCACTGTCTCTGCAGCCAAAACGACACCCCCATCTG

*TCTATCCACTGGCCCCTGGATCTGCTGCCCAAACTAACTCCATGGTGACCCTGGGATGCCTGGTCA*

*AGGGCTATTTCCCTGAGCCAGTGACAGTGACCTGGAACTCTGGATCCCTGTCCAGCGGTGTGCAC*

*ACCTTCCCAGCTGTCCTGCAGTCTGACCTCTACACTCTGAGCAGCTCAGTGACTGTCCCCTCCAGC*

*ACCTGGCCCAGCGAGACCGTCACCTGCAACGTTGCCCACCCGGCCAGCAGCACCAAGGTGGACA*

*AGAAAATTGTGCCCAGGGATTGTGGTTGTAAGCCTTGCATATGTACAGTCCCAGAAGTATCATCTGT*

*CTTCATCTTCCCCCCAAAGCCCAAGGATGTGCTCACCATTACTCTGACTCCTAAGGTCACGTGTGTT*

*GTGGTAGACATCAGCAAGGATGATCCCGAGGTCCAGTTCAGCTGGTTTGTAGATGATGTGGAGGTT*

*GCACACAGCTCAAACGCAACCCCGGGAGGAGCAGTTCAACAGCACTTTCCGCTCAGTCAGTGAAC*

*TTCCCATCATGCACCAGGACTGGCTCAATGGCAAGGAGTTCAAATGCAGGGTCAACAGTGCAGCTT*

*TCCCTGCCCCCATCGAGAAAACCATCTCCAAAACCAAAGGCAGACCGAAGGCTCCACAGGTGTAC*

*ACCATTCCACCTCCCAAGGAGCAAATGGCCAAGGATAAAGTCAGTCTGACCTGCATGATAACAGAC*

*TTCTTCCCTGAAGACATTACTGTGGAGTGGCAGTGGAATGGGCAGCCAGCGGAGAACTACAAGAA*

*CACTCAGCCCATCATGGACACAGATGGCTCTTACTTCGTCTACAGCAAGCTCAATGTGCAGAAGAG*

*CAACTGGGAGGCAGGAAATACTTTCACCTGCTCTGTGTTACATGAGGGCCTGCACAACCACCATAC*

*TGAGAAGAGCCTCTCCCACTCTCCTGGTAAATGA* (The italic region encodes the heavy chain
constant region.)

Light Chain of mAb7GW:
Amino Acid Sequence
(SEQ ID NO: 3)

<u>M D S Q A Q V L M L L L L W V S G S C G</u> D I V M S Q S P S S L A V S V G E K V T M S C K S S
    Signal peptide

Q S L L Y S R N Q K N Y L A W Y Q L K P G Q S P K L L I Y W A S T R E S G V P D R F T G
    CDR1                                                  CDR2

S G S G T D F T L T I S S V K A E D L A V Y Y C Q Q Y Y S Y P L T F G A G T K L E L K R A
                                                      CDR3

*D A A P T V S I F P P S S E Q L T S G G A S V V C F L N N F Y P K D I N V K W K I D G S E R Q N G*

*V L N S W T D Q D S K D S T Y S M S S T L T L T K D E Y E R H N S Y T C E A T H K T S T S P I V K S*

*F N R N E C* (The italic region refers to the light chain constant region.)

Nucleotide Sequence
(SEQ ID NO: 4)

<u>ATGGATTCACAGGCCCAGGTTCTTATGTTACTGCTGCTATGGGTATCTGGTTCCTGTGGGACA</u>
        Signal peptide

TTGTGATGTCACAGTCTCCATCCTCCCTAGCTGTGTCAGTTGGAGAGAAGGTTACTATGAGCT

GCAAGTCCAGTCAGAGCCTTTTATATAGTAGGAATCAAAAGAACTACTTGGCCT
                CDR1

GGTACCAGCTGAAGCCAGGGCAGTCTCCTAAACTGCTGATTTACTGGGCATCCACTAGG
                                                        CDR2

GAATCTGGGGTCCCTGATCGCTTCACAGGCAGTGGATCTGGGACAGATTTCACTCTCACCAT

CAGCAGTGTGAAGGCTGAAGACCTGGCAGTTTATTACTGTCAGCAATATTATAGCTA
                                                            CDR3

TCCGCTCACGTTCGGTGCTGGGACCAAGCTGGAGCTGAAACGGGCTGATGCTGCACCAACTG

*TATCCATCTTCCCACCATCCAGTGAGCAGTTAACATCTGGAGGTGCCTCAGTCGTGTGCTTCTTGAA*

*CAACTTCTACCCCAAAGACATCAATGTCAAGTGGAAGATTGATGGCAGTGAACGACAAAATGGCGT*

*CCTGAACAGTTGGACTGATCAGGACAGCAAAGACAGCACCTACAGCATGAGCAGCACCCTCACGT*

*TGACCAAGGACGAGTATGAACGACATAACAGCTATACCTGTGAGGCCACTCACAAGACATCAACTT*

*CACCCATTGTCAAGAGCTTCAACAGGAATGAGTGTTAG* (The italic region encodes the light chain -continued constant region.)

Heavy Chain of mAb51D:
Amino Acid Sequence
(SEQ ID NO: 5)

<u>MNFGLSLIFLALILKGVQC</u>EVQLVEAGGDLVKPGGSLKLSCAASGFSLSNYGMSWVRQTPDK
    Signal peptide                                    CDR1

RLEWVASISSGGRFTSYPDSVRGRFTISRDNAKNTLYLQMSGLKSEDTAMYYCARHDGNG
      CDR2                                                CDR3

GDYWGQGTSVTVSS*AKTTPPSVYPLAPGSAAQTNSMVTLGCLVKGYFPEPVTVTWNSGSLSSGVHTF*

*PAVLQSDLYTLSSSVTVPSSTWPSETVTCNVAHPASSTKVDKKIVPRDCGCKPCICTVPEVSSVFIFPPKP*

*KDVLTITLTPKVTCVVVDISKDDPEVQFSWFVDDVEVHTAQTQPREEQFNSTFRSVSELPIMHQDWLN*

*GKEFKCRVNSAAFPAPIEKTISKTKGRPKAPQVYTIPPPKEQMAKDKVSLTCMITDFFPEDITVEWQWN*

*GQPAENYKNTQPIMDTDGSYFVYSKLNVQKSNWEAGNTFTCSVLHEGLHNHHTEKSLSHSPGK* (The
italic region refers to the heavy chain constant region.)

Nucleotide Sequence
(SEQ ID NO: 6)

<u>ATGAACTTCGGGCTCAGCCTGATTTTCCTTGCCCTCATTTTAAAAGGTGTCCAGTGTGAGGTGC</u>
        Signal peptide

AGCTGGTGGAGGCTGGGGGAGACTTAGTGAAGCCTGGAGGGTCCCTGAAACTCTCCTGTGC

GGCCTCTGGATTCAGTTTGAGTAACTATGGCATGTCCTGGGTTCGCCAGACTCCAGA
                                CDR1

CAAGAGGCTGGAGTGGGTCGCAAGCATTAGTAGTGGTGGTCGTTTCACCTCCTATCC
                                                CDR2

AGACAGTGTGAGGGGGCGATTCACCATCTCCAGAGACAATGCCAAGAACACCCTGTACCT

GCAAATGAGCGGTCTGAAGTCTGAGGACACAGCCATGTATTACTGTGCAAGACACGACGGC

AACGGTGGGGACTACTGGGGTCAAGGAACCTCAGTCACCGTCTCCTCAGCCAAA
    CDR3

*ACGACACCCCCATCTGTCTATCCACTGGCCCCTGGATCTGCTGCCCAAACTAACTCCATGGTGACC*

*CTGGGATGCCTGGTCAAGGGCTATTTCCCTGAGCCAGTGACAGTGACCTGGAACTCTGGATCCCT*

*GTCCAGCGGTGTGCACACCTTCCCAGCTGTCCTGCAGTCTGACCTCTACACTCTGAGCAGCTCAGT*

*GACTGTCCCCTCCAGCACCTGGCCCAGCGAGACCGTCACCTGCAACGTTGCCCACCCGGCCAGC*

*AGCACCAAGGTGGACAAGAAAATTGTGCCCAGGGATTGTGGTTGTAAGCCTTGCATATGTACAGTC*

*CCAGAAGTATCATCTGTCTTCATCTTCCCCCCAAAGCCCAAGGATGTGCTCACCATTACTCTGACTC*

*CTAAGGTCACGTGTGTTGTGGTAGACATCAGCAAGGATGATCCCGAGGTCCAGTTCAGCTGGTTTG*

*TAGATGATGTGGAGGTGCACACAGCTCAGACGCAACCCCGGGAGGAGCAGTTCAACAGCACTTTC*

*CGCTCAGTCAGTGAACTTCCCATCATGCACCAGGACTGGCTCAATGGCAAGGAGTTCAAATGCAGG*

*GTCAACAGTGCAGCTTTCCCTGCCCCCATCGAGAAAACCATCTCCAAAACCAAAGGCAGACCGAAG*

*GCTCCACAGGTGTACACCATTCCACCTCCCAAGGAGCAGATGGCCAAGGATAAAGTCAGTCTGAC*

*CTGCATGATAACAGACTTCTTCCCTGAAGACATTACTGTGGAGTGGCAGTGGAATGGGCAGCCAGC*

*GGAGAACTACAAGAACACTCAGCCCATCATGGACACAGATGGCTCTTACTTCGTCTACAGCAAGCT*

*CAATGTGCAGAAGAGCAACTGGGAGGCAGGAAATACTTTCACCTGCTCTGTGTTACATGAGGGCCT*

*GCACAACCACCATACTGAGAAGAGCCTCTCCCACTCTCCTGGTAAATGA* (The italic region encodes
the heavy chain constant region.)

Light Chain of mAb51D:
Amino Acid Sequence
(SEQ ID NO: 7)

<u>MDFQVQIFSFLLISASVIMSRGQ</u>IVLSQFPAILSASPGEKVTMTCRARSSVSFMHWYQQKPGS
    Signal peptide                                   CDR1

SPKPWIYATSNLASGVPPRFSGSGSGTSYSLTISRVEAEDAATYYCQQWSSNIPYTFGGGTKLE
      CDR2                                           CDR3

-continued

IKRADAAPTVSIFPPSSEQLTSGGASVVCFLNNFYPKDINVKWKIDGSERQNGVLNSWTDQDSKDSTYS

*MSSTLTLTKDEYERHNSYTCEATHKTSTSPIVKSFNRNEC*
(The italic region refers to the light chain constant region)

Nucleotide Sequence (SEQ ID NO: 8)

ATGGATTTTCAAGTGCAGATTTTCAGCTTCCTGCTAATCAGTGCTTCAGTCATAATGTCCA
      Signal peptide

GAGGACAAATTGTTCTCTCCCAGTTTCCAGCAATCCTGTCTGCATCTCCAGGGGAGAAGGTC

ACAATGACTTGCAGGGCCAGGTCAAGTGTAAGTTTCATGCACTGGTACCAGCAGAA
        CDR1

GCCAGGATCCTCCCCCAAACCCTGGATTTATGCCACATCCAACCTGGCTTCTGGAGTCC
              CDR2

CTCCTCGCTTCAGTGGCAGTGGGTCTGGGACCTCTTACTCTCTCACAATCAGCAGAGTGGAG

GCTGAAGATGCTGCCACTTATTACTGCCAGCAGTGGAGTAGTAACCCATACACGTTC
           CDR3

GGAGGGGGGACTAAGCTGGAAATAAAACGGGCTGATGCTGCACCAACTGTATCCATCTTCCCA

*CCATCCAGTGAGCAGTTAACATCTGGAGGTGCCTCAGTCGTGTGCTTCTTGAACAACTTCTACCCC*

*AAAGACATCAATGTCAAGTGGAAGATTGATGGCAGTGAACGACAAAATGGCGTCCTGAACAGTTGG*

*ACTGATCAGGACAGCAAAGACAGCACCTACAGCATGAGCAGCACCCTCACGTTGACCAAGGACGA*

*GTATGAACGACATAACAGCTATACCTGTGAGGCCACTCACAAGACATCAACTTCACCCATTGTCAAG*

*AGCTTCAACAGGAATGAGTGTTAG*
(The italic region encodes the light chain constant region.)

A functional equivalent of mAb7GW or mAb51D has the same epitope-binding specificity as mAb7GW or mAb51D and exhibits at least 20% (e.g., 30%, 40%, 50%, 60%, 70%, 80%, 90%, or greater) of the activity of neutralizing a signaling pathway mediated by IL-19 and/or IL-20 as relative to mAb7GW or mAb51D. In some embodiments, a functional equivalent of mAb7GW or mAb51D contains the same regions/residues responsible for antigen-binding as mAb7GW or mAb51D, such as the same specificity-determining residues in the CDRs or the whole CDRs. The regions/residues that are responsible for antigen-binding can be identified from amino acid sequences of the heavy chain/light chain sequences of mAb7GW or mAb51D (shown above) by methods known in the art. See, e.g., www.bioinf.org.uk/abs; Almagro, J. Mol. Recognit. 17:132-143 (2004); and Chothia et al., J. Mol. Biol. 227:799-817 (1987).

In some examples, a functional equivalent (variant) of mAb7GW or mAb51D comprises a $V_H$ chain that includes a $V_H$ CDR1, $V_H$ CDR2, and $V_H$ CDR3 at least 75% (e.g., 80%, 85%, 90%, 95%, or 98%) identical to the corresponding $V_H$ CDRs of mAb7GW or mAb51D, and a $V_L$ chain that includes a $V_L$ CDR1, $V_L$ CDR2, and $V_L$ CDR3 at least 75% (e.g., 80%, 85%, 90%, 95%, or 98%) identical to the corresponding $V_H$ CDRs of mAb7GW or mAb51D.

Alternatively, the functional equivalent of mAb7GW or mAb51D comprises a $V_H$ chain at least 75% (e.g., 80%, 85%, 90%, 95%, or 98%) identical to the $V_H$ chain (mature or precursor) of mAb7GW or mAb51D and a $V_L$ chain at least 75% (e.g., 80%, 85%, 90%, 95%, or 98%) identical to the $V_L$ chain (mature of precursor) of mAb7GW or mAb51D.

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In other examples, a functional equivalent of mAb7GW or mAb51D comprises a $V_H$ chain that includes up to 5 (e.g., 1, 2, 3, 4, or 5) amino acid residue variations in the $V_H$ CDR regions ($V_H$ CDR1, CDR2, and/or CDR3) as compared to the $V_H$ CDRs of mAb7GW or mAb51D, and/or a $V_L$ chain that includes up to 5 (e.g., 1, 2, 3, 4, or 5) amino acid residue variations in the $V_L$ CDR regions ($V_L$ CDR1, CDR2, and/or CDR3) as compared to the $V_H$ CDRs of mAb7GW or mAb51D.

A functional equivalent of mAb7GW or mAb51D can be a genetically engineered antibody derived from one of the monoclonal antibodies (e.g., chimeric, single-chain, or humanized) via, e.g., routine recombinant technology.

Any of the anti-IL-20R1 antibodies described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made.

In one example, the anti-IL-20R1 antibody is a humanized antibody. A humanized antibody contains a human immunoglobulin (i.e., recipient antibody) in which regions/residues responsible for antigen binding (e.g., the complementarity determining regions, particularly the specificity-determining residues therein) are replaced with those from a non-human immunoglobulin (i.e., donor antibody). Methods to identify regions/residues in the heavy and light chains of an antibody are well known in the art. See, e.g., Almagro, J. Mol. Recognit. 17:132-143 (2004); and Chothia et al., J. Mol. Biol. 227: 799-817 (1987). In some instances, one or more residues inside a framework region of the recipient antibody are also replaced with those from the donor antibody. A humanized antibody may also contain residues from neither the recipient antibody nor the donor antibody. These residues are included to further refine and optimize antibody performance.

In another example, the anti-IL-20R1 antibody described herein is a chimeric antibody, which can include a heavy constant region and a light constant region from a human antibody. A chimeric antibody has a variable region or part of variable region from a first species and a constant region from a second species. Typically, in these chimeric antibodies, the variable region of both light and heavy chains mimics the variable regions of antibodies derived from one species of mammals (e.g., a non-human mammal), while the constant portions are homologous to the sequences in antibodies derived from another (e.g., human). In some embodiments, amino acid modifications can be made in the variable region and/or the constant region.

Methods of making various types of antibodies (e.g., monoclonal and polyclonal antibodies, antigen-binding fragments thereof, and genetically engineered antibodies), are well known in the art. See, for example, Harlow and Lane, (1988) Antibodies: A Laboratory Manual, Cold Spring Harbor Laboratory, New York.

In general, to produce antibodies against a protein (e.g., IL-20R1 or IL-20R2), the protein or a fragment thereof, optionally coupled to a carrier protein, such as KLH, can be mixed with an adjuvant, and injected into a host animal. Antibodies produced in the animal can then be purified by peptide affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

Polyclonal antibodies are present in the sera of the immunized subjects. Monoclonal antibodies can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies disclosed herein may be cultivated in vitro or in vivo. The ability to produce high titers of monoclonal antibodies in vivo makes it a particularly useful method of production.

Antigen-binding fragments of the just-mentioned IL-20 receptor neutralizing antibody can be prepared via routine methods. For example, F(ab')$_2$ fragments can be produced by pepsin digestion of an antibody molecule, and Fab fragments that can be generated by reducing the disulfide bridges of F(ab')$_2$ fragments.

Genetically engineered antibodies, such as humanized antibodies, chimeric antibodies, single-chain antibodies, and bi-specific antibodies, can be produced via conventional recombinant technology. Techniques developed for the production of "chimeric antibodies" can be used. See, e.g., Morrison et al. (1984) Proc. Natl. Acad. Sci. USA 81, 6851; Neuberger et al. (1984) Nature 312, 604; and Takeda et al. (1984) Nature 314:452.

Antibodies can also be humanized by methods known in the art. For example, a humanized antibodies can be designed as follows. First, the variable regions of $V_H$ and $V_L$ of a parent non-human antibody are subjected to three-dimensional molecular modeling analysis following methods known in the art. See, e.g., Queen et al., *Proc. Natl. Acad. Sci. USA*, 86:10029-10033 (1989). Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected. The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage scFv library and scFv clones specific to IL-20R1 or IL-20R2 can be identified from the library following routine procedures. Positive clones can be subjected to further screening to identify those that suppress IL-20 receptor activity.

After obtaining antibodies specific to the target antigen, their ability to neutralize the signaling pathway mediated by IL-19 and/or IL-20 can be determined by a routine procedure. For example, the level of IL-10 secretion induced by IL-19 in peripheral blood mononuclear cells is used as an indicator of IL-19/IL-20 receptor activity. In an example, IL-20 receptor activity can be determined by examining IL-19-induced caspase 3 and caspase 9 cleavage in renal epithelial cells. Antibodies that specifically binding to IL-20 receptor and suppressing its activity (e.g., neutralizing IL-20 receptor activated by IL-19) are selected for use in the methods disclosed herein.

Use of Anti-IL-20R Antibodies for Treating Allergic Airway Diseases

Any of the anti-IL-20R antibodies described herein can be formulated into a pharmaceutical composition, which further comprises one or more pharmaceutically acceptable carriers. "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof.

The pharmaceutically acceptable carriers, excipients, or stabilizers suitable for use in preparation of the just-noted pharmaceutical compositions can be in the form of lyophilized formulations or aqueous solutions. Remington: The Science and Practice of Pharmacy 20th Ed. (2000) Lippincott Williams and Wilkins, Ed. K. E. Hoover. They may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The pharmaceutical compositions as described herein can be formulated for storage by mixing an antibody having the desired degree of purity with optional pharmaceutically acceptable carriers, excipients or stabilizers mentioned above.

In some examples, the pharmaceutical compositions comprise liposomes encapsulating any of the antibodies described herein. Such liposomes can be prepared by methods known in the art. See, e.g., Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients (e.g., the antibody) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

In other examples, the pharmaceutical compositions can be formulated in sustained-release form. Suitable examples of sustained-release formulatons include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can also be prepared in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0.

The emulsion compositions can be those prepared by mixing an IL-20 antagonist with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

To practice the method disclosed herein, an effective amount of the pharmaceutical composition noted above can be administered to a subject (e.g., a human) in need of the treatment via a suitable route. The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having an allergic airway disorder, such as asthma, allergic rhinitis, allergic pneumonia, and bronchial airway obstruction. A subject having an allergic airway disorder can be identified by routine medical examination. A subject suspected of having an allergic airway disorder might show one or more symptoms of the disorder, e.g., wheezing, coughing, chest tightness, and shortness of breath. Such subjects can also be identified via routine medical examination. A subject at risk for an allergic airway disorder such as asthma can be a subject having one or more of the risk factors for that disorder. For example, risk factors associated with asthma include (a) having a family member such as a parent or sibling with asthma, (b) having allergic conditions, such as atopic dermatitis or allergic rhinitis (hay fever), (c) being overweight, (d) being a smoker or exposure to secondhand smoke, (e) Exposure to exhaust fumes or other types of pollution, (f) exposure to occupational triggers, such as chemicals used in farming, hairdressing and manufacturing, and (g) low birth weight.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of allergic airway disorders. Alternatively, sustained continuous release formulations of anti-IL-20R antibodies may be appropriate. Various formulations and devices for achieving sustained release are known in the art.

In one example, dosages for an IL-20R antibody may be determined empirically in individuals who have been given one or more administration(s) of anti-IL-20R antibodies. Individuals are given incremental dosages of the antibodies. To assess efficacy of the antibodies, an indicator of the allergic airway disorder (such as serum levels of IgE and/or IL-13) can be followed.

Generally, for administration of any of the antibodies described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate an allergic airway disorder (e.g., asthma) or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

For the purpose of the present disclosure, the appropriate dosage of an antibody will depend on the specific antibody (or compositions thereof) employed, the type and severity of the allergic airway disorder to be treated, whether the antibody is administered for preventive or therapeutic purposes, previous therapy, the patient's clinical history and response to the antibody, and the discretion of the attending physician. Typically the clinician will administer an IL-20R1 antibody until a dosage is reached that achieves the desired result. Administration of an antibody can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing an allergic airway disorder.

As used herein, the term "treating" refers to the application or administration of a composition including one or more active agents to a subject, who has an allergic airway disorder, a symptom of the disorder, or a predisposition toward the disorder, with the purpose to cure, heal, alleviate, relieve, alter, remedy, ameliorate, improve, or affect the disorder, the symptom of the disorder, or the predisposition toward the disorder.

In some embodiments, the antibody described herein that suppress the activation of IL-20 receptor via IL-19 and/or IL-20 is administered to a subject in need of the treatment at an amount sufficient to reduce the level of the IL-20 receptor/IL-19-mediated signaling and/or the level of the IL-20 receptor/IL-20-mediated signaling by at least 20% (e.g., 30%, 40%, 50%, 60%, 70%, 80%, 90% or greater). In other embodiments, the antibody is administered in an amount effective in reducing the serum IgE and/or IL-13 levels in the subject. In yet other embodiments, the antibody is administered in an amount effective in reducing the number of immune cells, particularly eosinophil and neutrophil cells, in the airway (BALF) of the subject.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In some embodiments, an anti-IL-20R antibody is administered via site-specific or targeted local delivery techniques, e.g., delivered to the airway of a patient. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

It is also apparent that an expression vector can be used to direct expression of any of the antibodies described herein (e.g., anti-IL-20R1 antibody). The therapeutic antibodies described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, i.e., dose, timing and repetition, used in the methods described herein will depend on the particular subject and that subject's medical history.

Kits for Use in Treating Allergic Airway Disorders

The present disclosure also provides kits for use in the instant methods. Kits of the invention include one or more containers comprising one or more of the anti-IL-20R antibodies described herein (e.g., a functional equivalent of mAb7GW or mAb51D as described above), and in some embodiments, further comprise instructions for use in accordance with any of the methods described herein. In some embodiments, the antibody is a full-length antibody or an antigen-binding fragment thereof. In other embodiments, the antibody contained in the kit is a humanized antibody or a chimeric antibody comprising human constant heavy and light chains.

When necessary, the kit can include instructions comprise a description of administration of the antibody to treat a target allergic airway disorder such as asthma according to any of the methods described herein. The kit may further comprise a description of selecting an individual suitable for the treatment based on identifying whether that individual has the target disorder. In still other embodiments, the instructions comprise a description of administering the antibody to an individual at risk of the target allergic airway disorder.

The instructions relating to the use of any of the antibodies described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating an allergic airway disorder, e.g. asthma, allergic rhinitis, allergic pneumonia, and bronchial airway obstruction. Instructions may be provided for practicing any of the methods described herein.

Any of the kits disclosed herein are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is one of the anti-IL-20R antibodies disclosed herein, such as monoclonal antibody mAb7GW, mAb51D, or a functional equivalent thereof.

Kits may optionally provide additional components such as buffers and interpretive information. Normally, the kit comprises a container and a label or package insert(s) on or associated with the container.

In some embodiments, the invention provides articles of manufacture comprising contents of the kits described above. In some embodiments, the kits comprise an IL-20 antagonist (such as anti-IL-20 antibody) with information indicating use to treat allergic airway disorders.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLE 1

IL-20R1 Knock-Out Mice did not Develop Asthma when Challenged with Allergen Der P IL-20R1 knock-out mice were constructed as described in US 2011/0256093, which is incorporated by reference in its entirety. Briefly, the exon 2 in mouse IL-20R1 gene was deleted via the traditional homologous recombination technology. The deletion of exon 2 was confirmed by Southern-blot using a DNA probe hybridizable to the 3' end of exon 2.

To induce allergic responses in the mouse airway, mice were anesthetized and administered with allergen Der P via nasal injection (i.p.) at the dosage of 25 µg/clay. Both wild type and IL-20R1 knock-out mice were treated in the same manner. The allergic response to the allergen was analyzed by counting total lymphocytes, eosinophil, and neutrophil accumulation in the airway.

To examine the lymphocytes in the airway of the IL-20R1 knock-out mice, the trachea of the mice was exposed and cannulated, and bronchoalveolar lavage (BAL) was performed with two aliquots of saline (1-mL each). If necessary, red blood cells were lysed following routine procedures. A total of 1.8 to 1.9 mL bronchoalveolar lavage fluid (BALF) was consistently recovered from each mouse by this technique. The lymphocytes in the BALF were harvested, suspended in a 1×HBSS buffer. The cell suspension was then centrifuged at 300 g for 10 minutes. After discarding the supernatant, the cells were suspended in RPM1640 medium. $10^5$ lymphocytes were cytospinned on a slide. The number of total lymphocytes was counted. The numbers of eosinophil cells and neutrophil cells were determined by Liu's staining and counted under the microscope.

As shown in FIG. 1, the total number of lymphocytes in the BALF of IL-20R1 knock-out mice was much lower than that in the BALF of wild-type mice.

Next, the serum levels of IgE and IL-13, two major players in allergic responses, in the knock-out mice were examined as follows. Serum samples were obtained from the blood of wild-type and knock-out mice. The levels of IgE and IL-13 in the serum samples were determined using the ELISA kit purchased from R& D, following the manufacture's (standard) protocol.

Figure 2:
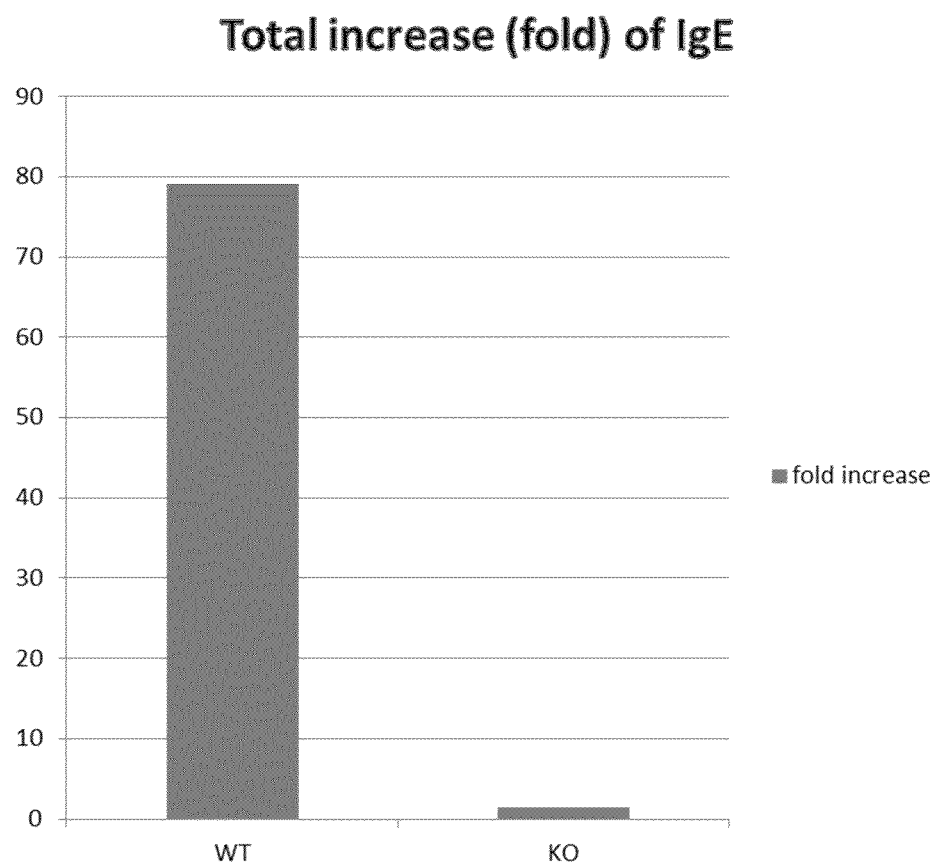
FIG. 2 is a chart showing the levels of IgE (panel A) and IL-13 (panel B) in WT and KO mice.
Figure 2:
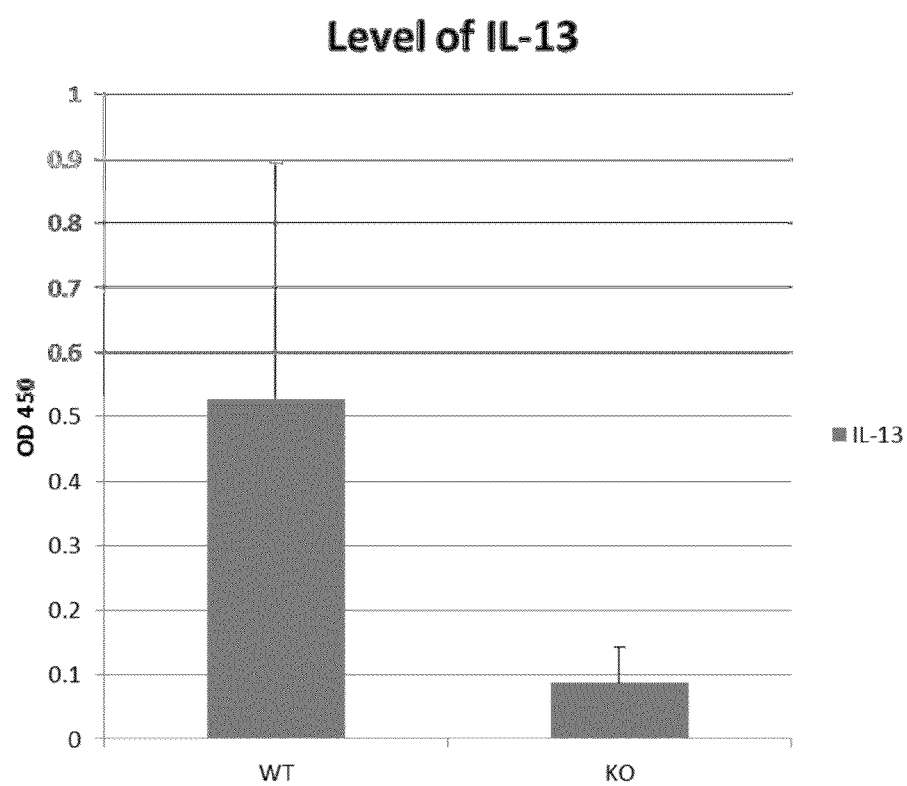

It was found that the levels of both serum IgE and IL-13 were significantly reduced in the IL-20R1 mice as compared to the wild-type mice. FIG. 2.

Taken together, this study indicates that IL-20R1 might be involved in the pathogenesis of allergic disease development in the airway.

EXAMPLE 2

Figure 5:
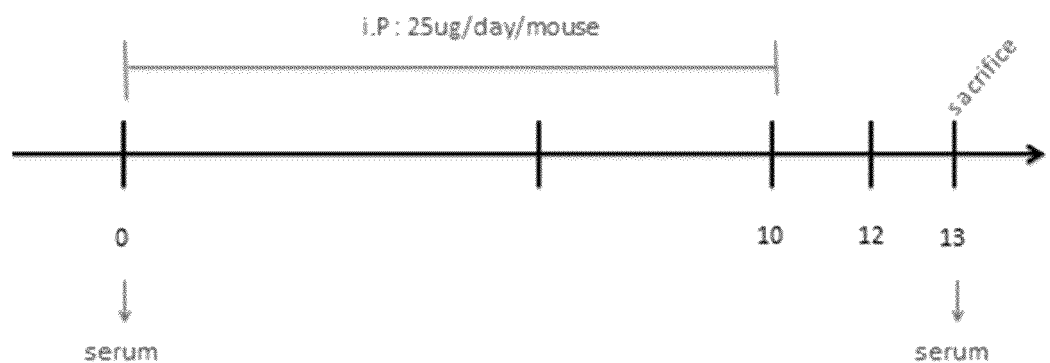
FIG. 5 is a schematic illustration showing the procedure of establishing a mouse allergy model.

An Anti-IL-20R1 Antibody Protected Mice from Developing Asthma in Response to Allergen Exposure To induce allergic responses in mouse airway, mice were anesthetized and administered with allergen Der P via nasal injection (i.p.) at the dosage of 25 µg/day for 10 days. See also FIG. 5. To examine the effects of mAb51D in the allergic mice induced with Der P, the mice were co-administered with mAb51D at 6 mg, mAb51D at 10 mg, a control mIgG. Untreated mice (native) were used as a blank control.

Three days after the treatment, the mice were sacrificed. Blood samples and BALF samples were collected following the methods described in Example 1 above. The serum levels of IgE and IL-13, as well as the amounts of lymphocytes, including eosinophil and neutrophil, were determined also following the methods described above.

Figure 3:
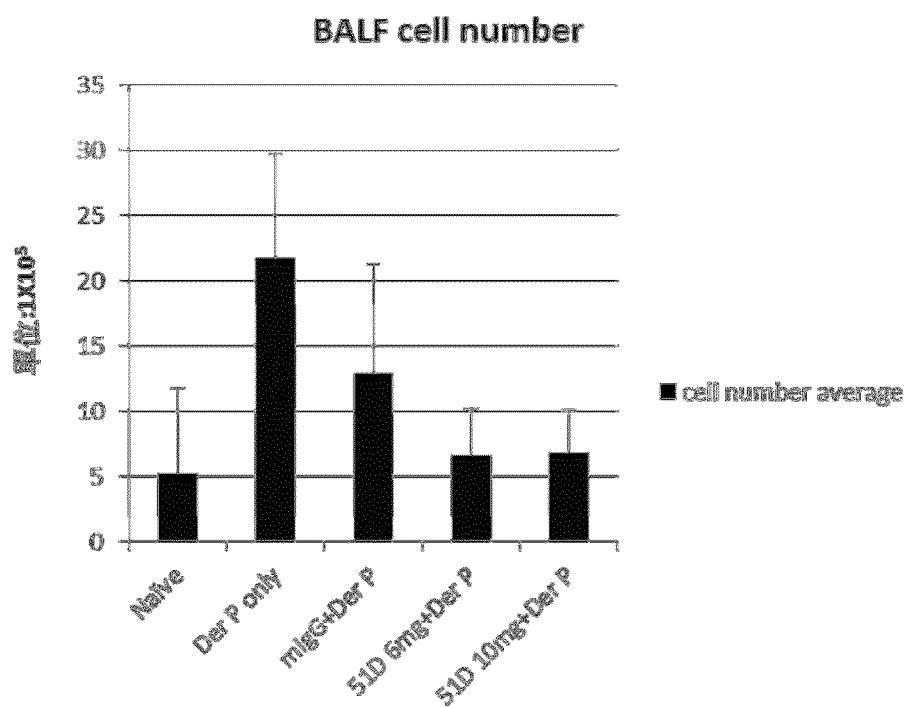
FIG. 3 is a chart showing the effects of mAb51D in reducing the numbers of total cells (panel A), eosinophil (panel B), and neutrophil (panel C) in the BALF of mice challenged with allergen Der P.
Figure 3:
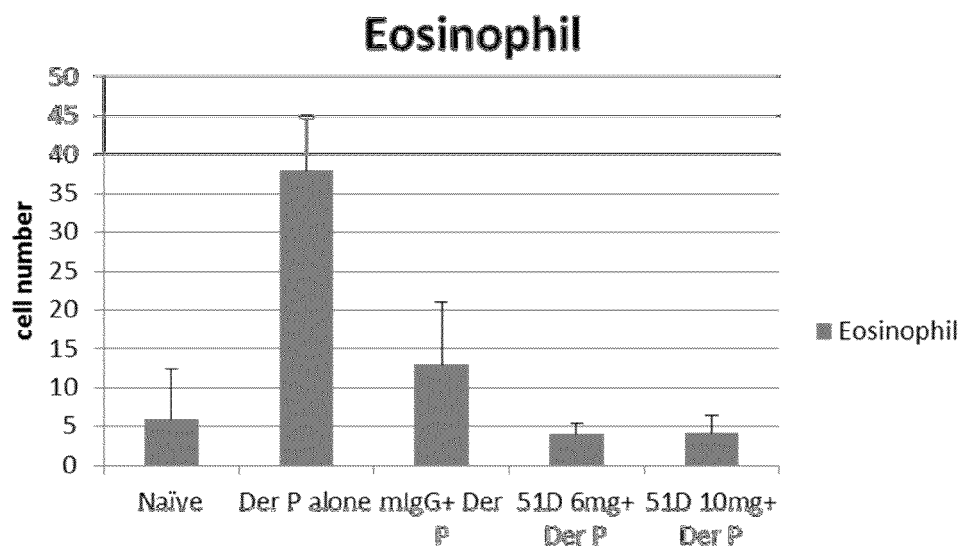
Figure 3:
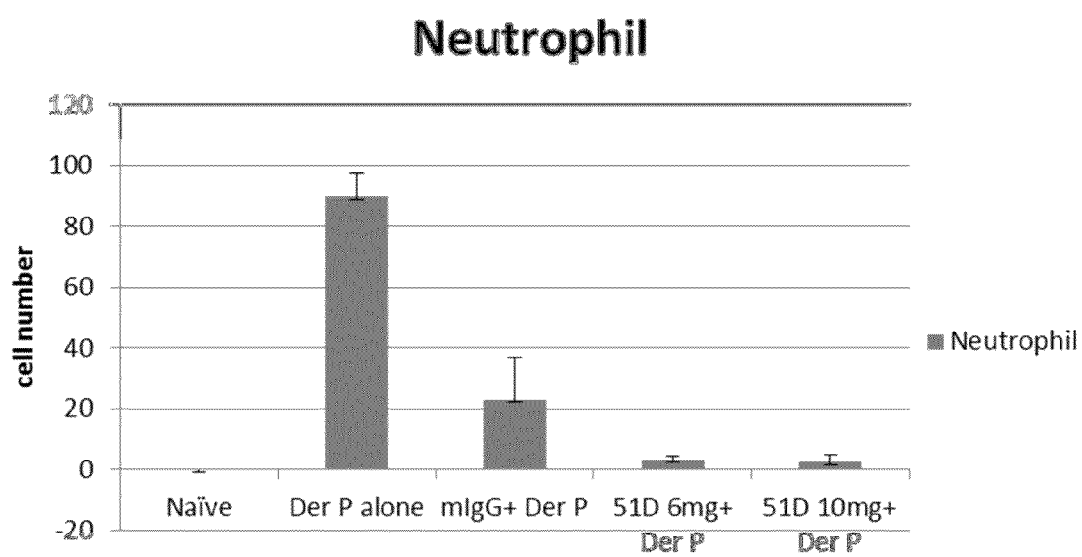
Figure 4:
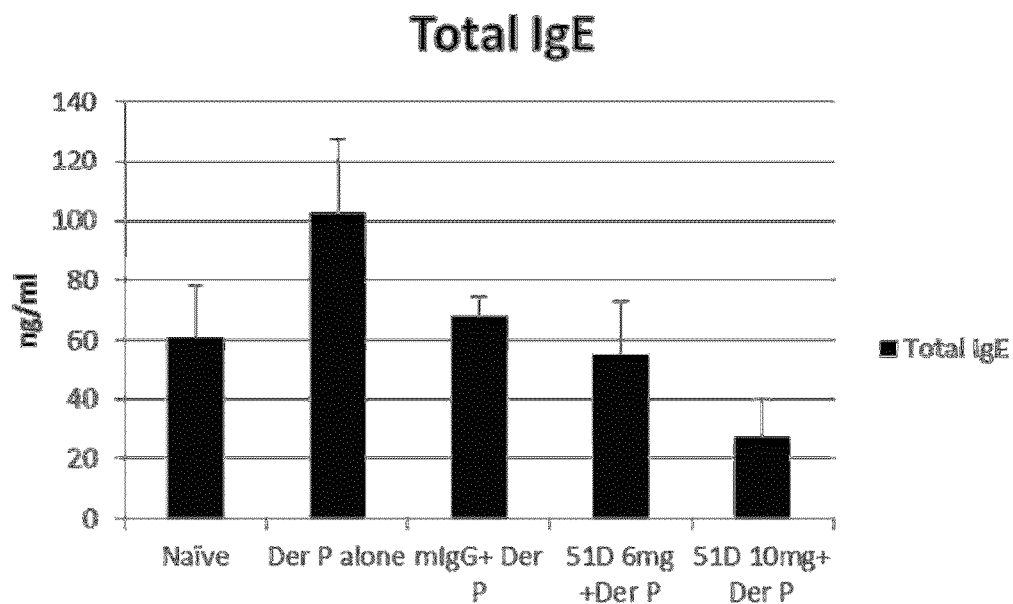
FIG. 4 is a chart showing the effects of mAb51D in reducing the serum levels of IgE (panel A) and IL-13 in mice challenged with allergen Der P (panel B).
Figure 4:
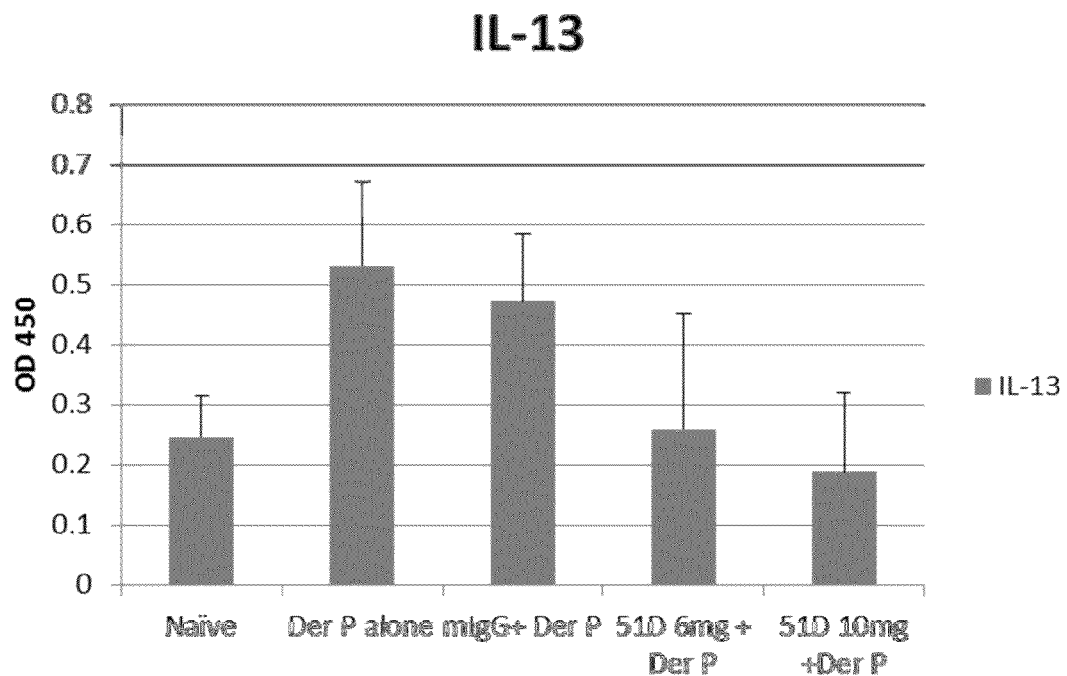

As shown in FIG. 3, panel A, mice challenged with Der p showed elevated levels of lymphocytes in BALF and mAb51D significantly reduced the number of BALF lymphocytes in the mice challenged with Der p. Similarly, mAb51D also significantly reduced the levels of eosinophil and neutrophil in the BALF of mice challenged by Der p (FIG. 3, panels B and C). Moreover, mAb51D significantly reduced the serum levels of IgE and IL-13 in mice challenged by Der p. FIG. 4. All these results indicate that mAb51D successfully neutralized the allergic responses induced by Der p, suggesting that anti-IL-20R1 antibodies would be effective in alleviating allergic responses in the airway of a subject in response to stimulations by allergens. As such, these antibodies can be used as therapeutic agents for treating allergic airway disorders such as asthma and bronchial airway obstruction.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for treating an allergic airway disorder, comprising administering to a subject in need thereof an effective amount of an anti-interleukin-20 receptor subunit 1 (anti-IL-20R1) antibody, wherein the anti-IL-20R1 antibody comprises:
   a heavy chain variable region ($V_H$) that includes a $V_H$ CDR1, a $V_H$ CDR2, and a $V_H$ CDR3 which are identical to the corresponding $V_H$ CDRs of mAb51D or mAb7GW, and
   a light chain variable region ($V_L$) that includes a $V_L$ CDR1, a $V_L$ CDR2, and a $V_L$ CDR3 which are identical to the corresponding $V_L$ CDRs of mAb51D or mAb7GW.

2. The method of claim 1, wherein the anti-IL-20R1 antibody comprises a $V_H$ that includes the same $V_H$ CDRs as those of mAb51D and a $V_L$ that includes the same $V_L$ CDRs as those of mAb51D.

3. The method of claim 1, wherein the anti-IL-20R1 antibody comprises a $V_L$ that includes the same $V_L$ CDRs as those of mAb7GW and a $V_H$ that includes the same $V_H$ CDRs as those of mAb7GW.

4. The method of claim 1, wherein the anti-IL-20R1 antibody comprises the same $V_H$ or $V_L$ as that of mAb51D or mAb7GW.

5. The method of claim 1, wherein the anti-IL-20R1 antibody is a full-length antibody or an antigen-binding fragment thereof.

6. The method of claim 5, wherein the antigen-binding fragment is Fab, F(ab')$_2$, Fab', or Fv.

7. The method of claim 1, wherein the anti-IL-20R1 antibody is a humanized antibody, a chimeric antibody, or a single-chain antibody.

8. The method of claim 1, wherein the allergic airway disorder is asthma.

9. The method of claim 8, wherein the anti-IL-20R1 antibody comprises a $V_H$ that includes the same $V_H$ CDRs as those of mAb51D and a $V_L$ that includes the same $V_L$ CDRs as those of mAb51D.

10. The method of claim 8, wherein the anti-IL-20R1 antibody comprises a $V_L$ that includes the same $V_L$ CDRs as those of mAb7GW and a $V_H$ that includes the same $V_H$ CDRs as those of mAb7GW.

11. The method of claim 8, wherein the anti-IL-20R1 antibody is a full-length antibody or an antigen-binding fragment thereof.

12. The method of claim 11, wherein the antigen-binding fragment is Fab, F(ab')$_2$, Fab', or Fv.

13. The method of claim 8, wherein the anti-IL-20R1 antibody is a humanized antibody, a chimeric antibody, or a single-chain antibody.

14. The method of claim 1, wherein the allergic airway disorder is bronchial airway obstruction.

15. The method of claim 1, wherein the anti-IL-20R1 antibody comprises a heavy chain variable region that is identical to the heavy chain variable region of mAb7GW or mAb51D, and a light chain variable region that is identical to the light chain variable region of mAb7GW or mAb51D.

16. The method of claim 8, wherein the anti-IL-20R1 antibody comprises a heavy chain variable region that is identical to the heavy chain variable region of mAb7GW or mAb51D, and a light chain variable region that is identical to the light chain variable region of mAb7GW or mAb51D.

* * * * *

SEQUENCE LISTING

```
<160> NUMBER OF SEQ ID NOS: 8

<210> SEQ ID NO 1
<211> LENGTH: 457
<212> TYPE: PRT
<213> ORGANISM: Mouse

<400> SEQUENCE: 1

Met Arg Val Leu Ile Leu Leu Trp Leu Phe Thr Ala Phe Pro Gly Ile
1               5                   10                  15

Leu Ser Val Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Tyr Ala Trp Asn Trp Ile Arg Gln Phe Pro Gly Asn Arg Leu
    50                  55                  60

Glu Trp Met Gly Tyr Ile Asp Tyr Ser Gly Ser Thr Lys Tyr Asn Pro
65                  70                  75                  80

Ser Leu Lys Ser Arg Ile Ser Val Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Ala Arg Asp Phe Gly Asp Ala Tyr Trp Gly Gln Gly Thr Leu
        115                 120                 125

Val Thr Val Ser Ala Ala Lys Thr Thr Pro Pro Ser Val Tyr Pro Leu
130                 135                 140

Ala Pro Gly Ser Ala Ala Gln Thr Asn Ser Met Val Thr Leu Gly Cys
145                 150                 155                 160

Leu Val Lys Gly Tyr Phe Pro Glu Pro Val Thr Val Thr Trp Asn Ser
                165                 170                 175

Gly Ser Leu Ser Ser Gly Val His Thr Phe Pro Ala Val Leu Gln Ser
            180                 185                 190

Asp Leu Tyr Thr Leu Ser Ser Ser Val Thr Val Pro Ser Ser Thr Trp
        195                 200                 205

Pro Ser Glu Thr Val Thr Cys Asn Val Ala His Pro Ala Ser Ser Thr
    210                 215                 220

Lys Val Asp Lys Lys Ile Val Pro Arg Asp Cys Gly Cys Lys Pro Cys
225                 230                 235                 240

Ile Cys Thr Val Pro Glu Val Ser Ser Val Phe Ile Phe Pro Pro Lys
                245                 250                 255

Pro Lys Asp Val Leu Thr Ile Thr Leu Thr Pro Lys Val Thr Cys Val
            260                 265                 270

Val Val Asp Ile Ser Lys Asp Asp Pro Glu Val Gln Phe Ser Trp Phe
        275                 280                 285

Val Asp Asp Val Glu Val His Thr Ala Gln Thr Gln Pro Arg Glu Glu
    290                 295                 300
```

```
Gln Phe Asn Ser Thr Phe Arg Ser Val Ser Glu Leu Pro Ile Met His
305                 310                 315                 320

Gln Asp Trp Leu Asn Gly Lys Glu Phe Lys Cys Arg Val Asn Ser Ala
            325                 330                 335

Ala Phe Pro Ala Pro Ile Glu Lys Thr Ile Ser Lys Thr Lys Gly Arg
            340                 345                 350

Pro Lys Ala Pro Gln Val Tyr Thr Ile Pro Pro Lys Glu Gln Met
            355                 360                 365

Ala Lys Asp Lys Val Ser Leu Thr Cys Met Ile Thr Asp Phe Pro
370                 375                 380

Glu Asp Ile Thr Val Glu Trp Gln Trp Asn Gly Gln Pro Ala Glu Asn
385                 390                 395                 400

Tyr Lys Asn Thr Gln Pro Ile Met Asp Thr Asp Gly Ser Tyr Phe Val
            405                 410                 415

Tyr Ser Lys Leu Asn Val Gln Lys Ser Asn Trp Glu Ala Gly Asn Thr
            420                 425                 430

Phe Thr Cys Ser Val Leu His Glu Gly Leu His Asn His His Thr Glu
            435                 440                 445

Lys Ser Leu Ser His Ser Pro Gly Lys
450                 455

<210> SEQ ID NO 2
<211> LENGTH: 1374
<212> TYPE: DNA
<213> ORGANISM: Mouse

<400> SEQUENCE: 2
atgagagtgc tgattctttt gtggctgttc acagcctttc ctggtatcct gtctgttgtg      60
cagcttcagg agtcgggacc tggcctggtg aaaccttctc agtctctgtc cctcacctgc     120
actgtcactg gctactcaat caccagtgat tatgcctgga ctggatccg gcagttcca     180 ggaaacagac tggagtggat gggctacata gactacagtg gtagcactaa atacaacccc     240
tctctcaaaa gtcgaatctc tgtcactcga gacacatcca agaaccagtt cttcctgcag     300
ttgaattctg tgactactga ggacacagcc acatatact gtgcaagaga ctttggtgat     360
gcttactggg gccaggggac tctggtcact gtctctgcag ccaaaacgac acccccatct     420
gtctatccac tggcccctgg atctgctgcc caaactaact ccatggtgac cctgggatgc     480
ctggtcaagg gctatttccc tgagccagtg acagtgacct ggaactctgg atccctgtcc     540
agcggtgtgc acaccttccc agctgtcctg cagtctgacc tctacactct gagcagctca     600
gtgactgtcc cctccagcac ctggcccagc gagaccgtca cctgcaacgt tgcccacccg     660
gccagcagca ccaaggtgga caagaaaatt gtgcccaggg attgtggttg taagccttgc     720
atatgtacag tcccagaagt atcatctgtc ttcatcttcc ccccaaagcc caaggatgtg     780
ctcaccatta tctgactcc taaggtcacg tgtgttgtgg tagacatcag caaggatgat     840
cccgaggtcc agttcagctg gtttgtagat gatgtggagg tgcacacagc tcaaacgcaa     900
ccccgggagg agcagttcaa cagcactttc cgctcagtca gtgaacttcc catcatgcac     960
caggactggc tcaatggcaa ggagttcaaa tgcagggtca acagtgcagc tttccctgcc    1020
cccatcgaga aaaccatctc caaaaccaaa ggcagaccga aggctccaca ggtgtacacc    1080
attccacctc ccaaggagca aatgccaag gataaagtca gtctgacctg catgataaca    1140
gacttcttcc ctgaagacat tactgtggag tggcagtgga tgggcagcc agcggagaac    1200 tacaagaaca ctcagcccat catggacaca gatggctctt acttcgtcta cagcaagctc    1260
```

```
aatgtgcaga agagcaactg ggaggcagga aatactttca cctgctctgt gttacatgag      1320
ggcctgcaca accaccatac tgagaagagc ctctcccact ctcctggtaa atga            1374
```

<210> SEQ ID NO 3
<211> LENGTH: 240
<212> TYPE: PRT
<213> ORGANISM: Mouse

<400> SEQUENCE: 3

```
Met Asp Ser Gln Ala Gln Val Leu Met Leu Leu Leu Leu Trp Val Ser
1               5                   10                  15

Gly Ser Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
        35                  40                  45

Leu Leu Tyr Ser Arg Asn Gln Lys Asn Tyr Leu Ala Trp Tyr Gln Leu
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro Leu Thr Phe Gly Ala Gly Thr
        115                 120                 125

Lys Leu Glu Leu Lys Arg Ala Asp Ala Ala Pro Thr Val Ser Ile Phe
    130                 135                 140

Pro Pro Ser Ser Glu Gln Leu Thr Ser Gly Gly Ala Ser Val Val Cys
145                 150                 155                 160

Phe Leu Asn Asn Phe Tyr Pro Lys Asp Ile Asn Val Lys Trp Lys Ile
                165                 170                 175

Asp Gly Ser Glu Arg Gln Asn Gly Val Leu Asn Ser Trp Thr Asp Gln
            180                 185                 190

Asp Ser Lys Asp Ser Thr Tyr Ser Met Ser Ser Thr Leu Thr Leu Thr
        195                 200                 205

Lys Asp Glu Tyr Glu Arg His Asn Ser Tyr Thr Cys Glu Ala Thr His
    210                 215                 220

Lys Thr Ser Thr Ser Pro Ile Val Lys Ser Phe Asn Arg Asn Glu Cys
225                 230                 235                 240
```

<210> SEQ ID NO 4
<211> LENGTH: 723
<212> TYPE: DNA
<213> ORGANISM: Mouse

<400> SEQUENCE: 4

```
atggattcac aggcccaggt tcttatgtta ctgctgctat gggtatctgg ttcctgtggg        60
gacattgtga tgtcacagtc tccatcctcc ctagctgtgt cagttggaga aaaggttact       120
atgagctgca agtccagtca gagcctttta tatagtagga tcaaaagaa ctacttggcc        180 tggtaccagc tgaagccagg gcagtctcct aaactgctga tttactgggc atccactagg       240
gaatctgggg tccctgatcg cttcacaggc agtggatctg gacagatttt cactctcacc       300
atcagcagtg tgaaggctga agacctggca gtttattact gtcagcaata ttatagctat       360
ccgctcacgt tcggtgctgg gaccaagctg gagctgaaac gggctgatgc tgcaccaact       420
```

```
gtatccatct tcccaccatc cagtgagcag ttaacatctg gaggtgcctc agtcgtgtgc     480
ttcttgaaca acttctaccc caaagacatc aatgtcaagt ggaagattga tggcagtgaa     540
cgacaaaatg gcgtcctgaa cagttggact gatcaggaca gcaaagacag cacctacagc     600
atgagcagca ccctcacgtt gaccaaggac gagtatgaac gacataacag ctataccctgt    660 gaggccactc acaagacatc aacttcaccc attgtcaaga gcttcaacag gaatgagtgt     720
tag                                                                   723
```

```
<210> SEQ ID NO 5
<211> LENGTH: 460
<212> TYPE: PRT
<213> ORGANISM: Mouse

<400> SEQUENCE: 5

Met Asn Phe Gly Leu Ser Leu Ile Phe Leu Ala Leu Ile Leu Lys Gly
1               5                   10                  15

Val Gln Cys Glu Val Gln Leu Val Glu Ala Gly Gly Asp Leu Val Lys
            20                  25                  30

Pro Gly Gly Ser Leu Lys Leu Ser Cys Ala Ala Ser Gly Phe Ser Leu
        35                  40                  45

Ser Asn Tyr Gly Met Ser Trp Val Arg Gln Thr Pro Asp Lys Arg Leu
    50                  55                  60

Glu Trp Val Ala Ser Ile Ser Ser Gly Gly Arg Phe Thr Ser Tyr Pro
65                  70                  75                  80

Asp Ser Val Arg Gly Arg Phe Thr Ile Ser Arg Asp Asn Ala Lys Asn
                85                  90                  95

Thr Leu Tyr Leu Gln Met Ser Gly Leu Lys Ser Glu Asp Thr Ala Met
            100                 105                 110

Tyr Tyr Cys Ala Arg His Asp Gly Asn Gly Gly Asp Tyr Trp Gly Gln
        115                 120                 125

Gly Thr Ser Val Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
```

```
                305                 310                 315                 320
Ile Met His Gln Asp Trp Leu Asn Gly Lys Glu Phe Lys Cys Arg Val
                    325                 330                 335

Asn Ser Ala Ala Phe Pro Ala Pro Ile Glu Lys Thr Ile Ser Lys Thr
                    340                 345                 350

Lys Gly Arg Pro Lys Ala Pro Gln Val Tyr Thr Ile Pro Pro Pro Lys
                    355                 360                 365

Glu Gln Met Ala Lys Asp Lys Val Ser Leu Thr Cys Met Ile Thr Asp
        370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                    405                 410                 415

Tyr Phe Val Tyr Ser Lys Leu Asn Val Gln Lys Ser Asn Trp Glu Ala
                    420                 425                 430

Gly Asn Thr Phe Thr Cys Ser Val Leu His Glu Gly Leu His Asn His
                    435                 440                 445

His Thr Glu Lys Ser Leu Ser His Ser Pro Gly Lys
        450                 455                 460

<210> SEQ ID NO 6
<211> LENGTH: 1383
<212> TYPE: DNA
<213> ORGANISM: Mouse

<400> SEQUENCE: 6
atgaacttcg ggctcagcct gattttcctt gccctcattt taaaggtgt  ccagtgtgag      60 gtgcagctgg tggaggctgg gggagactta gtgaagcctg agggtccct  gaaactctcc     120 tgtgcggcct ctggattcag tttgagtaac tatggcatgt cctgggttcg ccagactcca     180
gacaagaggc tggagtgggt cgcaagcatt agtagtggtg gtcgtttcac ctcctatcca     240
gacagtgtga gggggcgatt caccatctcc agagacaatg ccaagaacac cctgtacctg     300
caaatgagcg tctgaagtc tgaggacaca gccatgtatt actgtgcaag acacgacggc     360
aacggtgggg actactgggg tcaaggaacc tcagtcaccg tctcctcagc caaaacgaca     420
cccccatctg tctatccact ggcccctgga tctgctgccc aaactaactc catggtgacc     480
ctgggatgcc tggtcaaggg ctatttccct gagccagtga cagtgacctg aactctggga     540
tccctgtcca gcggtgtgca caccttccca gctgtcctgc agtctgacct ctacactctg     600
agcagctcag tgactgtccc ctccagcacc tggcccagcg agaccgtcac ctgcaacgtt     660
gcccacccgg ccagcagcac caaggtggac aagaaaattg tgcccaggga ttgtggttgt     720
aagccttgca tatgtacagt cccagaagta tcatctgtct tcatcttccc cccaaagccc     780
aaggatgtgc tcaccattac tctgactcct aaggtcacgt gtgttgtggt agacatcagc     840
aaggatgatc ccgaggtcca gttcagctgg tttgtagatg atgtggaggt gcacacagct     900
cagacgcaac cccgggagga gcagttcaac agcactttcc gctcagtcag tgaacttccc     960
atcatgcacc aggactggct caatggcaag gagttcaaat gcagggtcaa cagtgcagct    1020
ttccctgccc ccatcgagaa aaccatctcc aaaaccaaag cagaccgaa  ggctccacag    1080 gtgtacacca ttccacctcc caaggagcag atggccaagg ataaagtcag tctgacctgc    1140
atgataacag acttcttccc tgaagacatt actgtggagt ggcagtggaa tgggcagcca    1200
gcggagaact acaagaacac tcagcccatc atggacacag atggctctta cttcgtctac    1260
```

```
agcaagctca atgtgcagaa gagcaactgg gaggcaggaa atactttcac ctgctctgtg    1320
ttacatgagg gcctgcacaa ccaccatact gagaagagcc tctcccactc tcctggtaaa    1380
tga                                                                  1383
```

<210> SEQ ID NO 7
<211> LENGTH: 235
<212> TYPE: PRT
<213> ORGANISM: Mouse

<400> SEQUENCE: 7

```
Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Phe Pro Ala Ile
            20                  25                  30

Leu Ser Ala Ser Pro Gly Glu Lys Val Thr Met Thr Cys Arg Ala Arg
        35                  40                  45

Ser Ser Val Ser Phe Met His Trp Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Pro Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Tyr Thr Phe Gly Gly Gly Thr Lys Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235
```

<210> SEQ ID NO 8
<211> LENGTH: 708
<212> TYPE: DNA
<213> ORGANISM: Mouse

<400> SEQUENCE: 8

```
atggattttc aagtgcagat tttcagcttc ctgctaatca gtgcttcagt cataatgtcc      60
agaggacaaa ttgttctctc ccagtttcca gcaatcctgt ctgcatctcc aggggagaag     120
gtcacaatga cttgcagggc caggtcaagt gtaagtttca tgcactggta ccagcagaag     180
ccaggatcct cccccaaacc ctggatttat gccacatcca acctggcttc tggagtccct    240
cctcgcttca gtggcagtgg gtctgggacc tcttactctc tcacaatcag cagagtggag    300
gctgaagatg ctgccactta ttactgccag cagtggagta gtaacccata cacgttcgga    360
```

-continued

```
gggggggacta agctggaaat aaaacgggct gatgctgcac caactgtatc catcttccca      420
ccatccagtg agcagttaac atctggaggt gcctcagtcg tgtgcttctt gaacaacttc      480
taccccaaag acatcaatgt caagtggaag attgatggca gtgaacgaca aaatggcgtc      540
ctgaacagtt ggactgatca ggacagcaaa gacagcacct acagcatgag cagcaccctc      600
acgttgacca aggacgagta tgaacgacat aacagctata cctgtgaggc cactcacaag      660
acatcaactt cacccattgt caagagcttc aacaggaatg agtgttag                   708
```